US00PP13334P2

(12) United States Plant Patent
Kristiansen

(10) Patent No.: US PP13,334 P2
(45) Date of Patent: Dec. 10, 2002

(54) ASTER PLANT NAMED 'VICTORIA ELISABETH'

(75) Inventor: Kell Kristiansen, Årslev (DK)

(73) Assignee: Aster Klubben, Aarslev (DK)

( * ) Notice: Subject to any disclaimer, the term of this patent is extended or adjusted under 35 U.S.C. 154(b) by 0 days.

(21) Appl. No.: 10/077,375

(22) Filed: Feb. 15, 2002

(51) Int. Cl.[7] ..... A01H 5/00

(52) U.S. Cl. ..... Plt./355

(58) Field of Search ..... Plt./355

*Primary Examiner*—Kent L. Bell
(74) *Attorney, Agent, or Firm*—C. A. Whealy

(57) ABSTRACT

A distinct cultivar of Aster plant named 'Victoria Elisabeth', characterized by its upright and outwardly spreading plant habit; dark green foliage; freely flowering habit; and decorative-type inflorescences with red purple-colored ray florets.

1 Drawing Sheet

BOTANICAL CLASSIFICATION/CULTIVAR DESIGNATION

*Aster novi-belgii* cultivar 'Victoria Elisabeth'.

BACKGROUND OF THE INVENTION

The present Invention relates to a new and distinct cultivar of Aster plant, botanically known as *Aster novi-belgii* and hereinafter referred to by the name 'Victoria Elisabeth'.

The new Aster is a product of a planned breeding program conducted by the Inventor in Årslev, Denmark. The objective of the breeding program is to create new potted Aster cultivars with uniform plant growth habit, desirable floret colors, and good postproduction longevity.

The new Aster originated from a cross made by the Inventor in Årslev, Denmark, of a proprietary Aster selection identified as code number F1, not patented, as the female, or seed, parent with the Aster cultivar 'Loke Viking', disclosed in U.S. Plant Pat. No. 10,359, as the male, or pollen, parent. The new Aster was discovered and selected by the Inventor as a single flowering plant within the progeny of the stated cross grown in a controlled environment in Årslev, Denmark. The selection of this plant was based on its uniform plant growth habit and desirable inflorescence form and ray floret color.

Asexual reproduction of the new Aster by vegetative tip cuttings was first conducted in Årslev, Denmark during the Summer of 1999. Asexual reproduction by cuttings has shown that the unique features of this new Aster are stable and reproduced true to type in successive generations.

SUMMARY OF THE INVENTION

The cultivar 'Victoria Elisabeth' has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Victoria Elisabeth'. These characteristics in combination distinguish 'Victoria Elisabeth' as a new and distinct Aster:

1. Upright and outwardly spreading plant habit.
2. Dark green foliage.

3. Freely flowering habit.
4. Decorative-type inflorescences with red purple-colored ray florets.

Plants of the new Aster have more ray florets per inflorescence than plants of the female parent selection. In addition, plants of the new Aster differ from plants of the female parent selection in ray floret coloration.

Plants of the new Aster have more ray florets per inflorescence and have better postproduction longevity than plants of the male parent, the cultivar 'Loke Viking'. In addition, plants of the new Aster differ from plants of the cultivar 'Loke Viking' selection in ray floret coloration.

Plants of the new Aster can be compared to plants of the cultivar 'Kamma Viking', not patented. In side-by-side comparisons conducted in Broby, Denmark, plants of the new Aster differed from plants of the cultivar 'Kamma Viking' in the following characteristics:

1. Plants of the new Aster had shorter internodes than plants of the cultivar 'Kamma Viking'.
2. Plants of the new Aster were more freely flowering than plants of the cultivar 'Kamma Viking'.
3. Inflorescences of the new Aster had more ray florets than inflorescences of the cultivar 'Kamma Viking'.

BRIEF DESCRIPTION OF THE PHOTOGRAPHS

The accompanying colored photographs illustrate the overall appearance of the new Aster showing the colors as true as it is reasonably possible to obtain in colored reproductions of this type. Colors in the photographs may differ from the color values cited in the detailed botanical description which accurately describe the colors of the new Aster.

The photograph at the top of the sheet comprises a side perspective view of a typical flowering plant of 'Victoria Elisabeth'.

The photograph at the bottom of the sheet comprises a close-up view of typical inflorescences and leaves of 'Victoria Elisabeth'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Broby, Denmark, in a glass-covered greenhouse and under conditions which approximate those generally used in commercial potted Aster production. During the production of these plants, day and night temperatures averaged 21° C. One cutting was planted in 10-cm containers and pinched once. Plants were about 12 weeks old when the photographs and the botanical description were taken. Measurements and numerical values represent averages of typical flowering plants.

Botanical classification: *Aster novi-belgii* cultivar 'Victoria Elisabeth'.

Parentage:

*Female, or seed, parent.*—Proprietary *Aster novi-belgii* selection identified as code number F1, not patented.

*Male, or pollen, parent.*—*Aster novi-belgii* cultivar 'Loke Viking', disclosed in U.S. Plant Pat. No. 10,359.

Propagation:

*Type.*—Terminal tip cuttings.

*Time to initiate roots.*—Summer: About 12 days at 21° C. Winter: About 13 days at 21° C.

*Root description.*—White, close to 155D; fine; fibrous.

*Rooting habit.*—Freely branching.

Plant description:

*Appearance.*—Herbaceous decorative-type potted Aster. Stems upright and outwardly spreading. Appropriate for 10 to 15-cm containers.

*Plant height.*—About 20 cm.

*Plant width.*—About 24 cm.

*Lateral branches* (*peduncles*).—Length: About 15 cm. Diameter: About 3 mm. Strength: Strong. Angle: About 45° from vertical. Texture: Slightly pubescent. Color: 137C.

*Foliage description.*—Arrangement: Alternate; sessile. Length: About 4.5 cm. Width: About 1.2 cm. Shape: Lanceolate. Apex: Acute. Base: Cuneate. Margin: Entire with ciliation. Texture, upper and lower surfaces: Glabrous, smooth; leathery. Color: Young and mature foliage, upper surface: 147A; venation, close to 147A. Young and mature foliage, lower surface: 137C; venation, close to 137C.

Inflorescence description:

*Appearance.*—Decorative-type inflorescence form with narrowly obovate-shaped ray florets. Inflorescences terminal or axillary. Disc and ray florets arranged acropetally on a capitulum. Not fragrant. Inflorescences persistent.

*Flowering response.*—Under natural conditions, plants flower in the summer in Broby, Denmark.

*Postproduction longevity.*—Inflorescences maintain good color and substance for about three weeks on the plant in an interior environment.

*Quantity of inflorescences.*—About nine to thirteen inflorescences develop per lateral branch.

*Inflorescence bud.*—Length: About 8.5 mm. Diameter: About 7.5 mm. Shape: Ovoid. Color: Close to 147A.

*Inflorescence size.*—Diameter: About 3 cm. Depth (height): About 1.25 cm. Diameter of disc: About 4.5 mm.

*Ray florets.*—Shape: Narrowly obovate. Orientation: Intially upright, then horizontal to the peduncle. Aspect: Slightly recurved; straight to slightly concave. Length: About 1.1 cm. Width: About 1.5 mm. Apex: Rounded. Base: Attenuate. Margin: Entire. Texture, upper and lower surfaces: Smooth, glabrous. Number of ray florets per inflorescence: About 155 arranged in more than six rows. Color: When opening, upper and lower surfaces: 80A. Fully expanded, upper surface: 80A, fading to 80C with development. Fully expanded, lower surface: 80C.

*Disc florets.*—Arrangement: Massed at center of receptacle. Shape: Tubular, elongated. Apex: Acute. Length: About 1.5 mm. Width: Less than 1 mm. Number of disc florets per inflorescence: About 15 to 25. Color: Close to 150D.

*Phyllaries.*—Quantity per inflorescence: About 35 to 45. Length: About 2 mm. Width: Less than 1 mm. Shape: Narrowly obovate. Apex: Acuminate. Base: Truncate. Texture, upper and lower surfaces: Smooth. Color, upper and lower surfaces: 137B.

*Reproductive organs.*—Androecium: Present on disc florets only. Quantity per disc floret: One. Anther shape: Narrowly obovate. Anther length: About 2 mm. Anther color: 12A. Pollen amount: Moderate. Pollen color: 12A. Gynoecium: Present on both ray and disc florets. Pistil quantity per floret: One. Stigma shape: Bifurcate. Stigma color: 155A.

*Seed.*—Seed production has not been observed.

Disease/pest resistance: Resistance to pathogens and pests common to Asters has not been observed on plants grown under commercial greenhouse conditions.

It is claimed:

1. A new and distinct cultivar of Aster plant named 'Victoria Elisabeth', as illustrated and described.

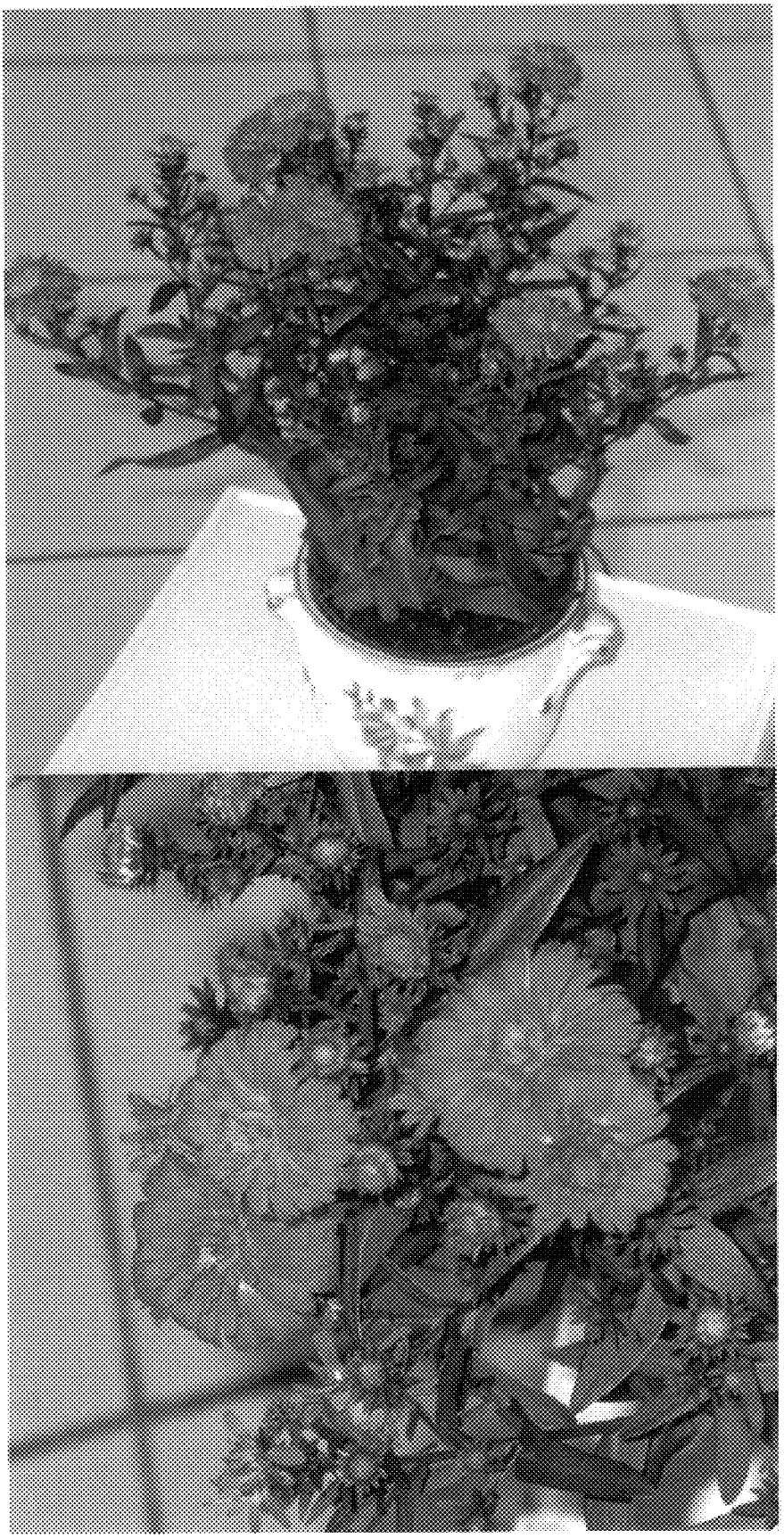

* * * * *